US006905704B2

(12) United States Patent
Osajima et al.

(10) Patent No.: US 6,905,704 B2
(45) Date of Patent: Jun. 14, 2005

(54) PEPTIDE SY (75) Inventors: Katsuhiro Osajima, Ehime (JP); Yasunori Ooishi, Ehime (JP)

(73) Assignee: Senmi Ekisu Co., Ltd., Ohzu (JP)

( * ) Notice: Subject to any disclaimer, the term of this patent is extended or adjusted under 35 U.S.C. 154(b) by 0 days.

(21) Appl. No.: 10/472,062

(22) PCT Filed: Dec. 24, 2002

(86) PCT No.: PCT/JP02/13441
§ 371 (c)(1),
(2), (4) Date: Sep. 16, 2003

(87) PCT Pub. No.: WO03/055901
PCT Pub. Date: Jul. 10, 2003

(65) Prior Publication Data
US 2004/0087504 A1 May 6, 2004

(30) Foreign Application Priority Data
Dec. 25, 2001 (JP) .......................... 2001-392758

(51) Int. Cl.[7] .......................... A23L 1/305; A61K 38/55; C07K 1/20; C07K 5/062; C07K 14/46
(52) U.S. Cl. .......................... 424/439; 426/657; 514/2; 514/21; 530/300; 530/344; 530/857
(58) Field of Search .............................. 530/300, 344, 530/857; 514/2, 21; 424/439; 426/657

(56) References Cited

U.S. PATENT DOCUMENTS

| 4,853,231 A | 8/1989 | Osajima et al. ............ 426/7 |
| 4,981,699 A | 1/1991 | Inada et al. ............... 426/7 |

FOREIGN PATENT DOCUMENTS

| EP | 445606 | 9/1991 |
| EP | 1094071 | 4/2001 |
| JP | 5-271297 | 10/1993 |
| JP | 6-239897 | 8/1994 |
| JP | 6-248000 | 9/1994 |
| JP | 7-215889 | 8/1995 |
| JP | 11-228599 | 8/1999 |

OTHER PUBLICATIONS

Hideharu Seki et al., "Iwashi Tanpakushitsu Yurai Sardine Peptide no Ketsuatsu Koka Sayo to Riyo no Genjo", Food Processing, Sep., 2000, vol. 35, No. 9, pp. 63 to 64.

Matsuda H. et al., Angiotensin I Converting Enzyme Inhibitory Peptides Generated from Sardin Muscle by Protease for Food Industry. Nippon Shokuhin Kogyo Gakkaishi vol. 39, No. 8, (1992), pp. 678 to 683.

Ukeda H et al., Peptides from Peptic Hydrolyzate of Heated Sardine Meat That Inhibit Angiotensin I Converting Enzyme. Nippon Nogeikagaku Kaishi vol. 66, No. 1 (1992), pp. 25 to 29.

(Continued)

*Primary Examiner*—Jeffrey Edwin Russel
(74) *Attorney, Agent, or Firm*—Oblon, Spivak, McClelland, Maier & Neustadt, P.C.

(57) ABSTRACT

Peptide SY is produced by applying a mixture of peptides obtained by processing fish meat with a protease to a peptide-adsorbing resin (ODS resin or the like), eluting this with water, then with a 11 to 18% v/v ethanol aqueous solution and further with water, and collecting and mixing a latter fraction of the water elution (1), a fraction of the 11 to 18 % v/v ethanol elution and a fraction of the water elution (2). Further, peptide SY-MD is produced by isolating only the fraction of the 11 to 18% v/v ethanol elution. Peptide SY and peptide SY-MD are both novel peptide mixtures. They not only contain a large amount of blood pressure-depressing peptide Val-Tyr newly found but also have less bitterness and are excellent in taste and stability, and can be used as a blood pressure-depressing agent or as functional foods for inhibiting blood pressure elevation or preventing blood pressure elevation.

8 Claims, 8 Drawing Sheets

OTHER PUBLICATIONS

The Journal of Biological Chemistry, vol. 255, No. 2, pp. 401–407 1980.

Abstract of the Report in the Congress of Japan Society for Bioscience, Biotechnology, and Agrochemistry (with English translation) vol. 67, No. 3, 1993.

Extract of the 21$^{st}$ Annual Sciencem Eeting of the Japanese Society of Hypertension (with English translation), 1998.

Journal of Hypertension, vol. 16, supple. 2, Jun. 1998, Abstracts 11Z.3 and P17.43.

J Jpn Soc Nutr Food Sci, vol. 52, pp. 271–277 1999 (with partial English translation).

Hideharu Seki et al., "Iwashi Tanpakushitsu Yurai Sardine Peptide no Ketsuatsu Koka Sayo to Riyo no Genjo", Food Processing, Sep., 2000, vol. 35, No. 9, pp. 63 to 64.

Matsuda H. et al., Angiotensin I Converting Enzyme Inhibitory Peptides Generated from Sardin Muscle by Protease for Food Industry. Nippon Shokuhin Kogyo Gakkaishi vol. 39, No. 8, (1992), pp. 678 to 683.

Ukeda H et al., Peptides from Peptic Hydrolyzate of Heated Sardine Meat That Inhibit Angiotensin I Converting Enzyme. Nippon Nogeikagaku Kaishi vol. 66, No. 1 (1992), pp. 25 to 29.

Retention time (min)

PEPTIDE SY

TECHNICAL FIELD OF WHICH THE INVENTION BELONGS

The present invention relates to novel peptide SY, and blood pressure-depressing agents and blood pressure-depressing functional foods in which peptide SY is used for blood pressure depression. Further, it relates to peptide SY-MD contained in peptide SY and a method for separating the same.

PRIOR ART

The present inventors previously succeeded in developing novel peptide α-1000 having an ACE (Angiotensin I-converting enzyme)-inhibiting activity by thermally denaturing fish meat, inactivating the autolytic enzyme, hydrolyzing it with a protease, inactivating the enzyme and then separating peptide α-1000, and have already obtained its patent right (Patent No. 3117779: JP-A-5-271297).

PROBLEMS THAT THE INVENTION IS TO SOLVE

With the increase of life-style related diseases, the new development of novel components effective for preventing triggering of hypertension or for depressing blood pressure has been in demand among those skilled in the art, and the invention has been made to meet the demand of those skilled in the art.

MEANS FOR SOLVING THE PROBLEMS

The present inventors have conducted investigations from various aspects for attaining the foregoing object. Consequently, the present inventors have focused again on ACE-inhibiting peptide α-1000 developed by them, and have assiduously made studies on various fractions. As a result, they have found for the first time that a fraction having a higher content of dipeptide Val-Tyr exhibits a higher ACE-inhibiting activity, and have identified that this Val-Tyr is one of main components of blood pressure-depressing peptides.

On the basis of the foregoing new useful finding, they have decided to freshly develop a new mixture of peptides which is not only high in Val-Tyr content but also has less bitterness and is also excellent in taste and stability, and have conducted a process in which a mixture of peptides (namely, peptide α-1000) obtained by processing fish meat with a protease is treated with a peptide-adsorbing resin (ODS resin) and subjected to three step elution, namely, water elution, elution with an ethanol aqueous solution and water elution. Then, they have obtained a useful new finding that most of Val-Tyr in fish meat peptides is recovered in the latter fraction of the first water elution, the fraction of the 11 to 18% v/v ethanol aqueous solution elution and the fraction of the last water elution.

Thus, it has been confirmed that a mixture of the latter fraction of the first water elution, the fraction of the 11 to 18% v/v ethanol aqueous solution elution and the fraction of the last water elution is a completely novel blood pressure-depressing mixture of peptides which is not only high in Val-Tyr content, but also has less bitterness and is excellent in taste and also in stability. This has been identified as a novel mixture of peptides, and here designated peptide SY.

Further, in the invention, only the fraction of the 11 to 18% v/v ethanol aqueous solution elution has been isolated and examined. Then, a new mixture of peptides having quite a low Na content of from 0.1 to 0.2% (in peptide SY, an Na content is from 1 to 3%) has been obtained, and this fraction has been designated peptide SY-MD.

In the invention, studies have been made for continuously recovering a mixture of peptides having as high a Val-Tyr content as possible using peptide α-1000 as a starting material.

Consequently, after treating peptide α-1000 with an ODS resin, a part of a fraction (latter fraction) eluted with the addition of water is obtained, and a fraction eluted with the addition of an ethanol aqueous solution is then obtained successively. At this time, it has been found that since a part of water used in the water elution (1) remains, the ethanol concentration is from 11 to 18% v/v, preferably from 14 to 16% v/v.

Further, when obtaining peptide SY, a time of starting collection in collecting the intended latter fraction of the water elution (1), a time of terminating the same (namely, a water elution (2) have been specified or judged respectively by measurement or monitoring of a fractionation time, a salt content, Bx and UV absorption at wavelength of 280 nm to establish a process for producing peptide SY by a certain continuous system. On the basis of these useful new findings, further studies have been made. At last, the invention has been completed.

The physicochemical properties of peptide SY of the invention are shown below.

Figure 2:
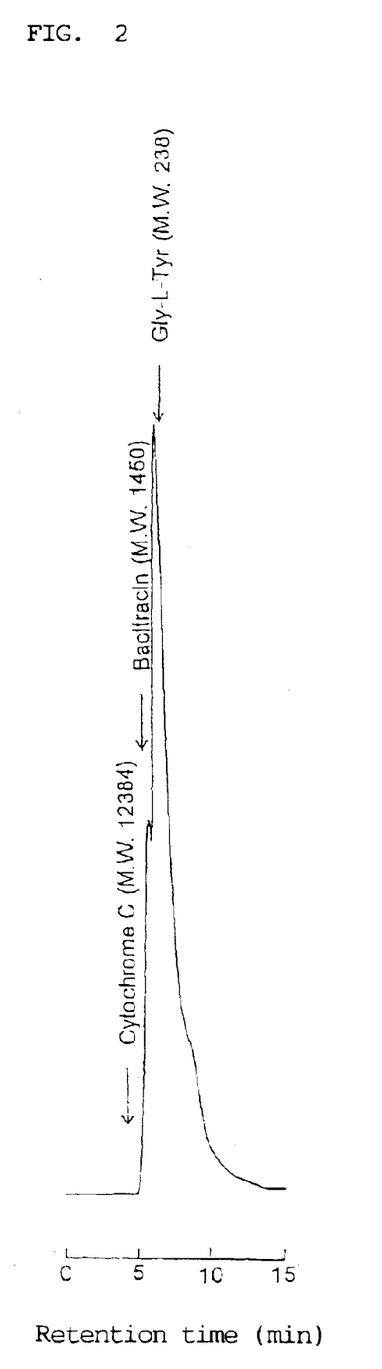
FIG. 2 shows a molecular weight of peptide SY.

Physicochemical Properties of Peptide SY (A) Molecular weight:

200 to 10,000 (measured by high-performance liquid chromatography: ASAHIPAK GS-320): FIG. 2

(B) Melting point: Colored and decomposed at 138±3° C.

(C) Solubility in solvents:

Easily soluble in water, but almost insoluble in ethanol, acetone and hexane.

(D) Appearance:

White or pale yellow powder.

(E) Liquid condition (pH): 4.0 to 6.0

(F) Components:

water 1 to 5% w/w (normal-pressure, heat-drying method)

protein 84 to 94% w/w (Micro-Kjeldahl method)

lipid 0.5% w/w or less (Soxhlet extraction method)

ash 4±2% w/w (direct ashing method)

(G) Physiological properties:

Containing dipeptide Val-Tyr and having an ACE-inhibiting activity.

Figure 3:
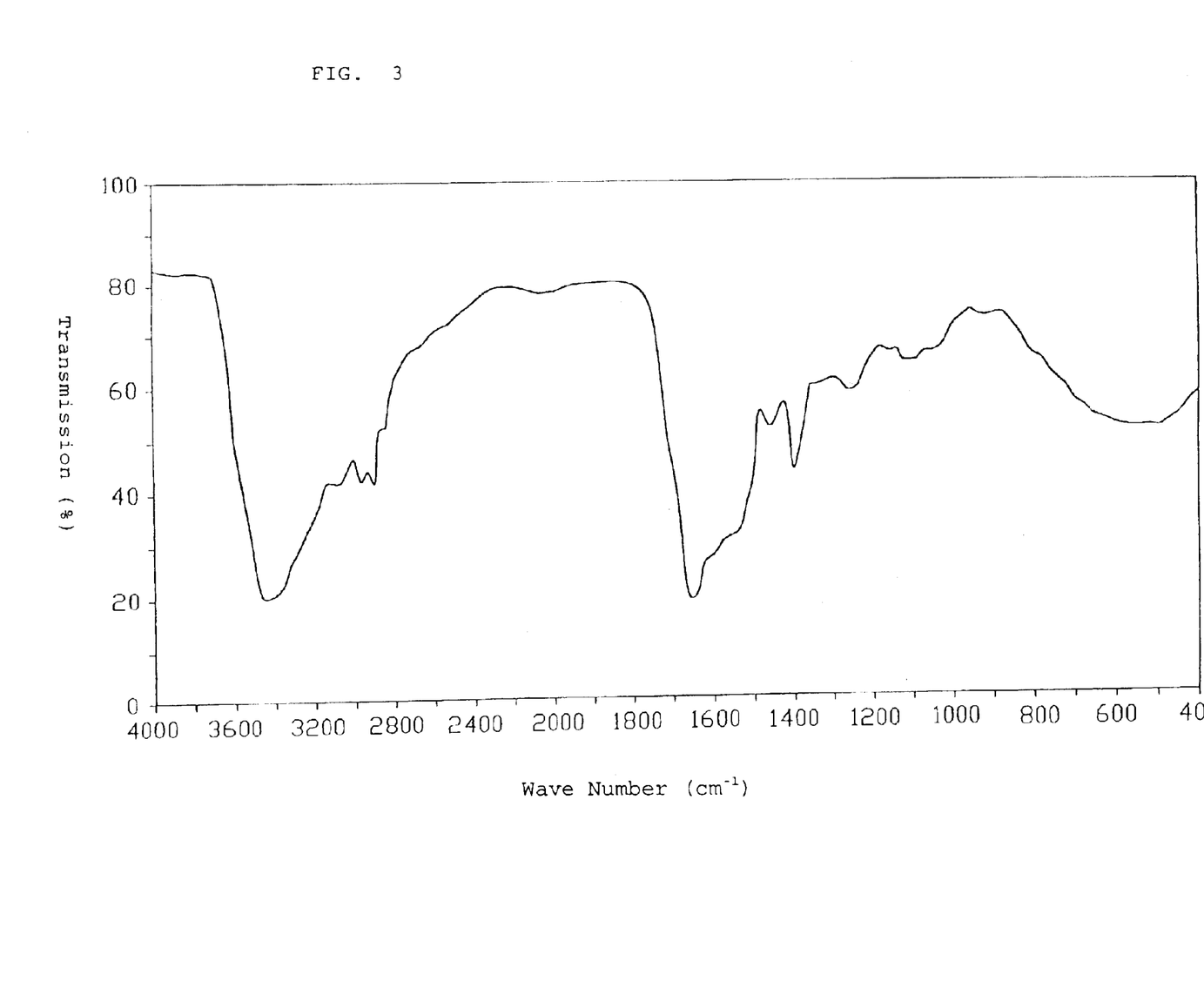
FIG. 3 shows an infrared absorption spectrum of peptide SY.

(H) Infrared absorption spectrum: FIG. 3

Figure 4:
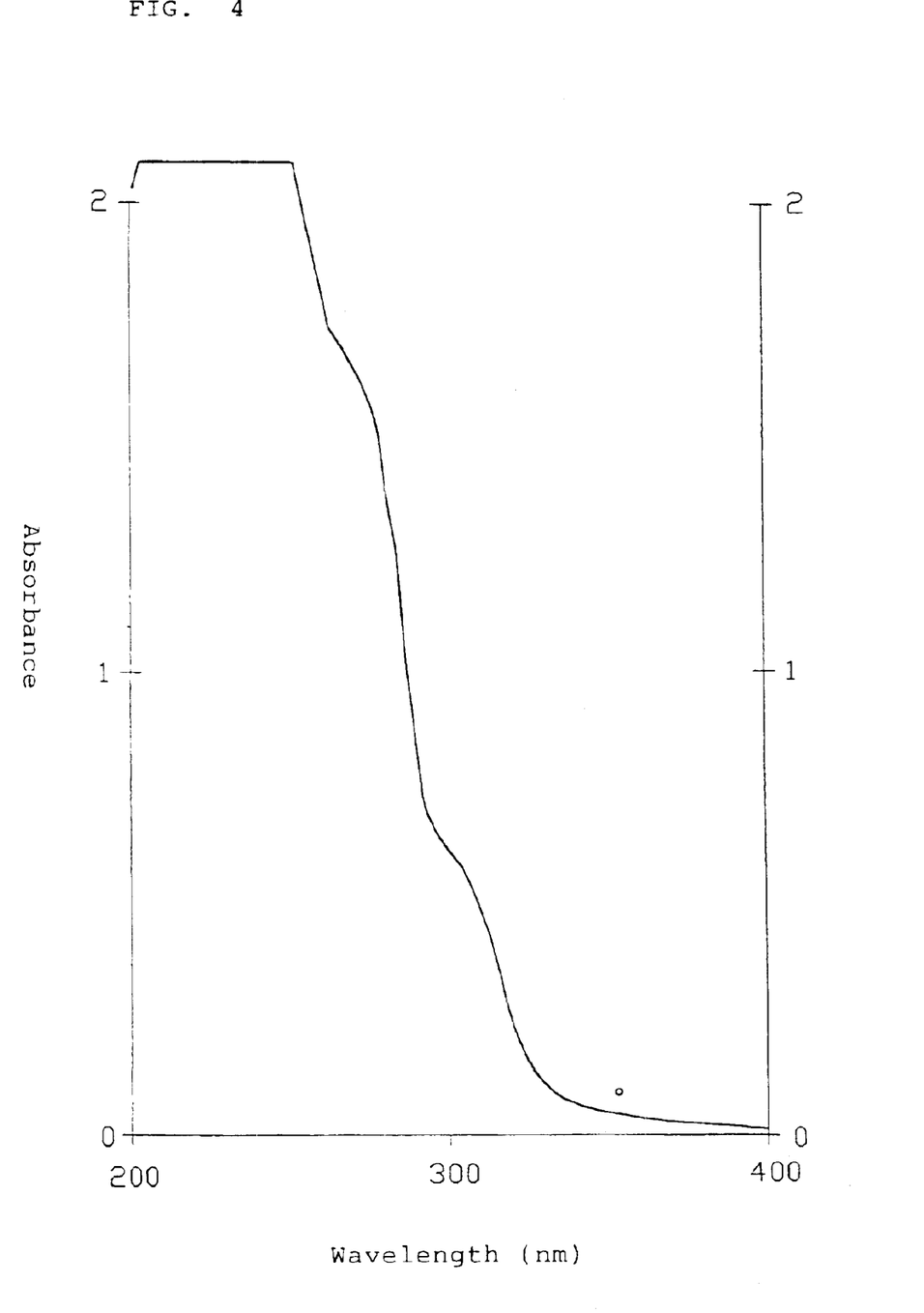
FIG. 4 shows an ultraviolet absorption spectrum of peptide SY.

(I) Ultraviolet absorption spectrum: FIG. 4

(J) Specific rotatory powder:

$[\alpha]_D^{20}=-40°$ to $-51°$

Peptide SY of the invention is produced as follows.

Figure 1:
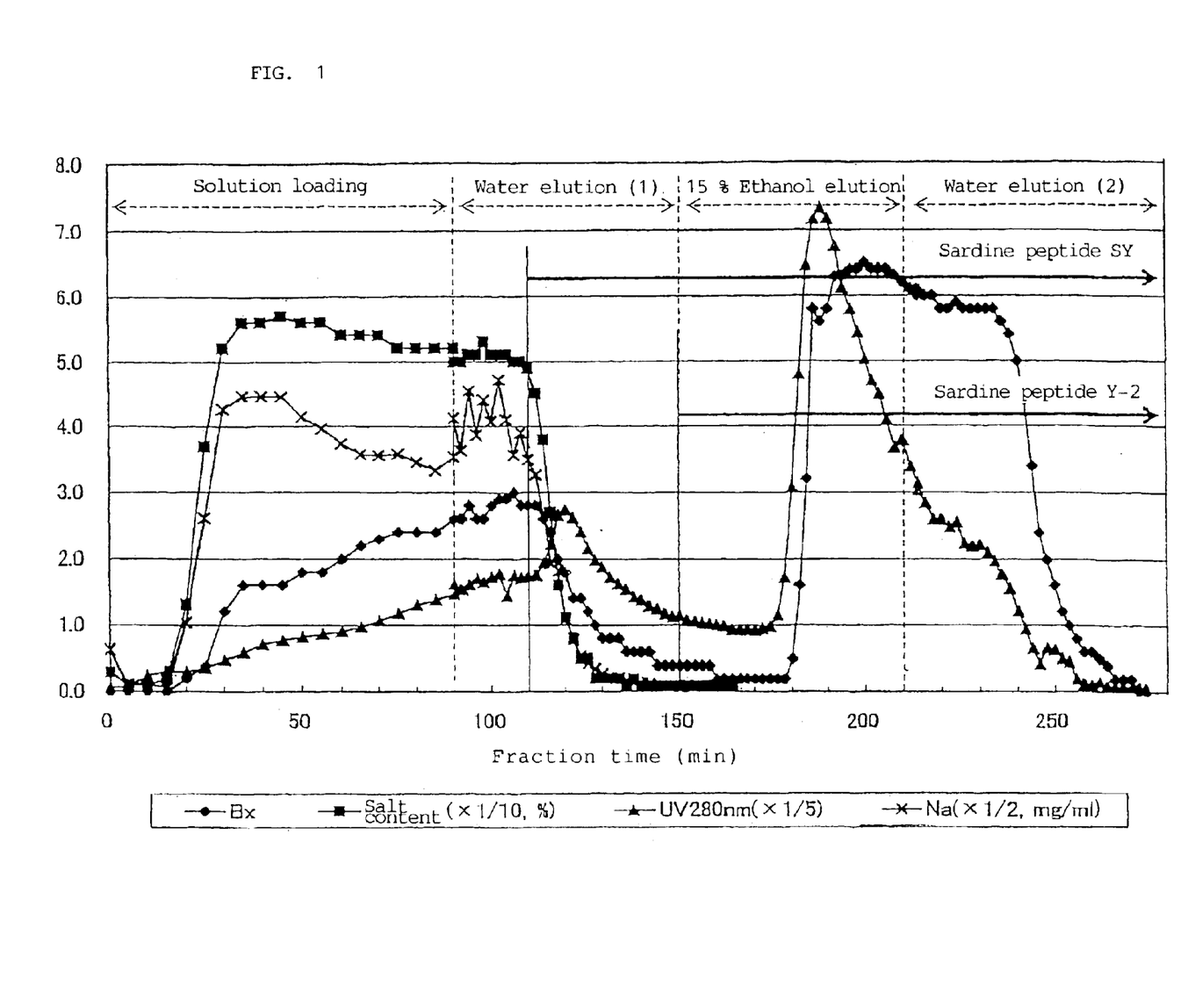
FIG. 1 is a graph showing a peptide SY elution pattern in Example 1.

That is, peptide SY is produced by collecting and mixing peptide components resulting from elution fractionation of a peptide solution with a peptide-adsorbing resin using water, an ethanol aqueous solution and water in this order as eluents of the elution fractionation, in which the peptide components are, in an elution pattern shown in FIG. 1, a latter fraction of the water elution (1), a fraction of the 11 to 18% v/v ethanol elution (elution with 15% ethanol is shown in FIG. 1) and a fraction of the water elution (2) obtained by the respective eluents as defined below.

(1) Latter fraction of the water elution (1): Fraction obtained using water as an eluent from a time when a sodium (Na) content of peptide (peptide SY) in the water elution (1) is from 1 to 3 g/100 g to a final collection time of the latter fraction in the water elution (1) when the sodium content is substantially 0 g/100 g.

(2) Fraction of the 11 to 18% v/v ethanol elution: Fraction obtained next using the ethanol aqueous solution having a concentration of 11 to 18% v/v as an eluent until an amount of peptides eluted is past the peak and reduced to approximately a half of the peak. (only this fraction is isolated and designated peptide SY-MD.)

(3) Fraction of the water elution (2): Fraction thereafter obtained using water as an eluent until the elution fractionation is completed.

Peptide α-1000 which is a starting material of peptide SY of the invention is described below.

Peptide α-1000 is produced using fishes and shellfishes as raw materials. For example, it can be produced according to Patent No. 3117779. First, fishes and shellfishes are processed in meat collectors, deboners or the like to separate their meat. It is desirable that the raw materials areas fresh as possible. The fish meat separated is ground and divided into plural lumps of ground fish meat weighing approximately 10 kg each, and these meat lumps may be subjected as such to the next treatment. It is also advisable that they are rapidly frozen with a spray of cold air of between −20 and −50° C., for example, approximately −30° C., and stored at between −20 and −25° C. and they are used as occasion demands.

As the fishes and shellfishes, fishes with red flesh, such as sardine, saurel, tuna, bonito, saury and mackerel, fishes with white flesh, such as flounder, sea bream, sillaginoid, gizzard shad, cod, herring and yellowtail, cartilaginous fishes such as shark and ray, freshwater fishes such as pond smelt, carp, char and "yamame" (a kind of trout), and deep-sea fishes such as granulose and anglerfish, shrimp, crab, octopus, opossum shrimp and the like can properly be used.

The fish and shellfish meat collected is ground with a meat grinder or the like, and water is added in an amount of from ½ to 20 times, preferably from 1 to 10 times the raw material by weight. Then, this is heat-treated to thereby inactivate the autolytic enzyme, kill bacteria and thermally denature the protein, whereby the efficiency of the subsequent enzymatic reaction is increased. As heating conditions, any conditions can be used so long as such functions are brought forth. For example, the conditions are 65° C. or more and from 2 to 60 minutes, preferably 80° C. or more and from 5 to 30 minutes.

Next, an alkaline agent such as aqueous ammonia or an aqueous solution of sodium (potassium) hydroxide is added thereto to adjust pH to an appropriate value of a protease to be used (for example, pH of 7.5 or more, preferably 8 or more for an alkali protease). The meat is heated at a temperature appropriate for an enzyme (it varies with an enzyme to be used, but it is from 20 to 65° C.; from 35 to 60° C., preferably from 40 to 55° C. for an alkali protease), and treated with the addition of a protease for from 30 minutes to 30 hours (from 30 minutes to 25 hours, preferably from 1 to 17 hours for an alkali protease).

Enzymes capable of degrading a protein in neutral or alkaline conditions can all be used as a protease either singly or in combination. Proteases can be derived not only from animals and vegetables but also from microorganisms. Pepsin, renin, trypsin, chymotrypsin, papain and bromelain, as well as bacterial proteases, filamentous proteases, actinomycelial proteases and the like can widely be used. These enzymes are generally available in the market. Depending on their purposes, unpurified enzymes and solid or liquid enzyme-containing substances such as enzyme-containing cultures and koji can also be used. The amount of the enzyme to be added may be between 0.1% and 5.0%.

As required, the meat is neutralized, and then retained at a temperature of 70° C. (preferably 80° C.) or more for from 2 to 60 minutes (preferably from 5 to 30 minutes) to inactivate the enzyme and facilitate the subsequent separation. After the inactivation by heating, coarse impurities are separated with a vibro-screen or the like, and the resulting product is treated with a Jector as required, and then subjected to ultracentrifugation to remove the floating impurities and the precipitated impurities.

Then, the product is filtered using a filter aid of diatomaceous earth or the like (for example, Celite), and the filtrate is processed with activated carbon (in an amount of from 0.05 to 20% w/v, preferably from 0.1 to 10% w/v; from 20 to 65° C., preferably from 25 to 60° C.; from 15 minutes to 4 hours, preferably from 30 minutes to 2 hours) to deodorize, decolor and purify it.

This product is concentrated (to approximately 30 Bx) in a usual manner, for example, under reduced pressure (from 0 to 50° C.). As required, this is then subjected again to (ultra)centrifugation or filtration to obtain a peptide solution. The thus-obtained peptide solution is sterilized (through UHTST (Ultra High Temperature Short Time; a kind of sterilizer) or in any other usual manner), and then filled in containers to provide a product (α-1000 (liquid)). As required, this can also be further concentrated or rather diluted, or may be powdered into a powdery product of 60-mesh or so in a usual manner, for example, by spray-drying or freeze-drying, and the powder may be packed in containers such as bags to provide a product (α-1000 (powder)). Of these products, the liquid product is chilled or frozen and stored, and the powdery product is stored in a dry cold, dark place.

The thus-obtained liquid, pasty or powdery peptide is α-1000.

The physicochemical properties of peptide α-1000 (spray-dried powder) are as shown below.

Physicochemical Properties of Peptide α-1000 (Powder)

(A) Molecular weight;

200 to 10,000 (measured by Sephadex G-25 column chromatography)

(B) Melting point;

Colored at 119° C. (decomposition point).

(C) Specific rotatory power;
$[\alpha]_D^{20} = -22°$ (D) Solubility in solvents;
Easily soluble in water; almost insoluble in ethanol, acetone and hexane.

(E) Differentiation in acidic, neutral or basic character;
Neutral, pH of from 6.0 to 8.0 (10% aqueous solution)

Figure 5:
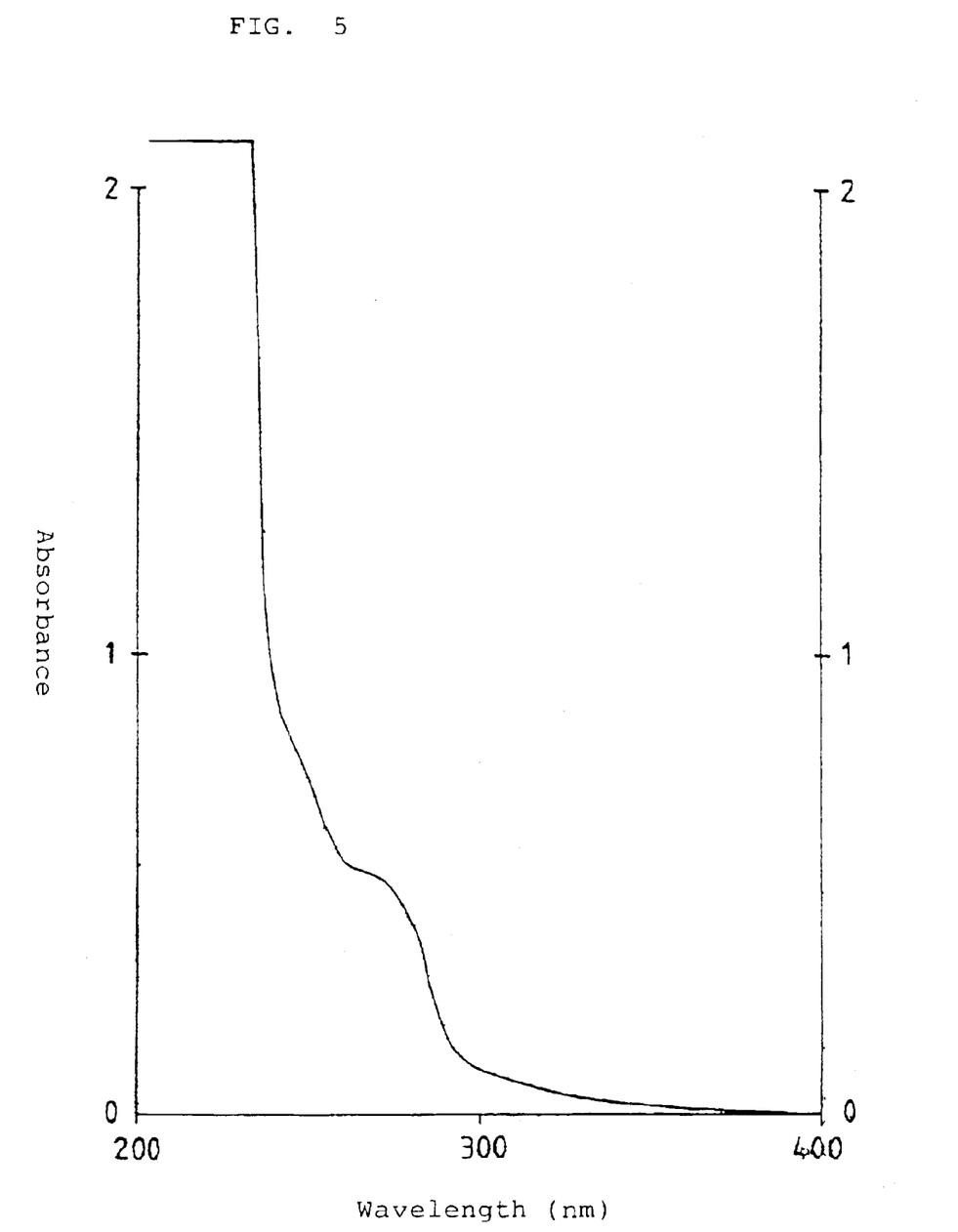
FIG. 5 shows an ultraviolet absorption spectrum of peptide α-1000.

(F) Ultraviolet absorption spectrum: FIG. 5

Figure 6:
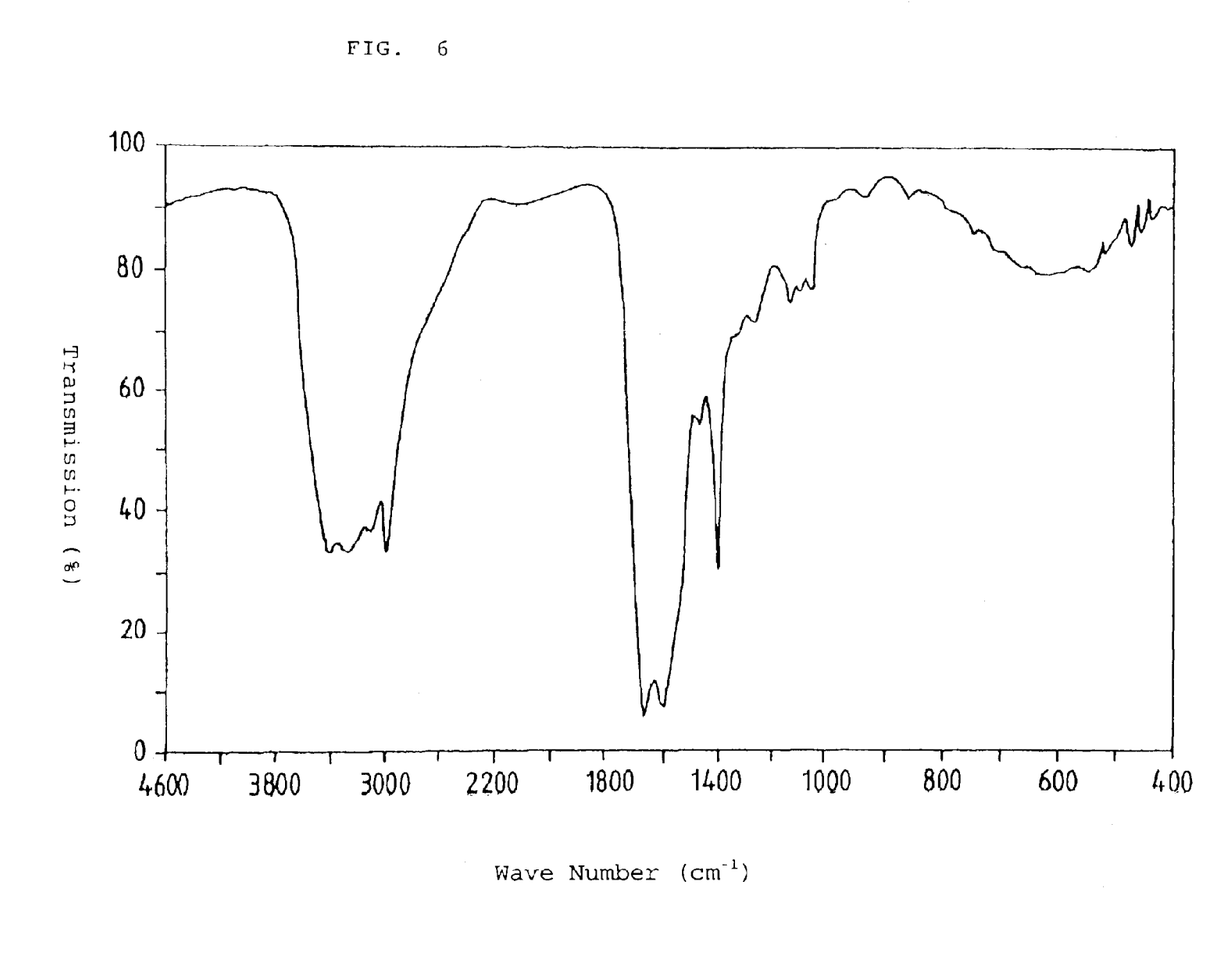
FIG. 6 shows an infrared absorption spectrum of peptide α-1000.

(G) Infrared absorption spectrum: FIG. 6

(H) Appearance, Components;
White powder; water 5.14% (reduced-pressure, heat-drying method); protein 87.5% (Kjeldahl method with a nitrogen/protein conversion coefficient of 6.25); lipid 0% (Soxhlet extraction method); ash 5.0% (direct ashing method)

(I) Characteristic;
Mixture of peptides derived from fish meat and obtained by heating the fish meat to inactivate its autolytic enzyme and hydrolyzing the resulting meat with a protease.

(J) Composition of amino acids;
As shown below.

| Items in analytical test All amino acids | Results (%) |
|---|---|
| arginine | 3.34 |
| lysine | 6.86 |
| histidine | 3.34 |
| phenylalanine | 2.33 |
| tyrosine | 2.01 |
| leucine | 6.35 |
| isoleucine | 3.27 |
| methionine | 2.26 |
| valine | 4.16 |
| alanine | 5.17 |
| glycine | 3.59 |
| proline | 2.15 |
| glutamic acid | 12.35 |
| serine | 3.30 |
| threonine | 3.70 |
| aspartic acid | 8.36 |
| tryptophan | 0.32 |
| cystine | 0.47 |
| total amount | 73.33 |

Analytical method: Measured by an amino acid automatic analytical method (provided cystine was measured by being oxidized with performic acid and then hydrolyzed with hydrochloric acid. Tryptophan was measured by high-performance liquid chromatography).

The thus-obtained peptide α-1000 is applied to a peptide-adsorbing resin such as an ODS resin or the like directly when liquid, or after adding water when powdery to perform "solution loading" shown in FIG. 1. Incidentally, with respect to the resin, all types of resins are available so long as they are peptide-adsorbing resins. For example, various ODS resins, YMC ODS-AQ 120-S50 (trade name) and a hydrophobic adsorbing resin SEPABEADS SP207 (trade name for a product of Mitsubishi Chemical Corporation) are used as required.

As a result of studies from various aspects regarding a mixture of peptides which has a high Val-Tyr content and less bitterness and excellent in taste and stability among pressure-depressing mixtures of peptides (for example, α-1000) formed by processing fish meat with a protease, the invention has succeeded for the first time in collecting the intended fractions from the foregoing various fractions and mixing them. The novel pressure-depressing mixture of peptides thus formed by collecting and mixing the fractions has been designated peptide SY.

Peptide SY can be produced by collecting the fractions from the foregoing eluted fractions. An example of an elution pattern of the eluates is shown in FIG. 1.

Peptide SY according to the invention can be produced, as shown in FIG. 1, by adding, for example, α-1000 to the peptide-adsorbing resin (solution loading), then carrying out elution with water (water elution (1)), and mixing a latter fraction of the water elution (1), a fraction of a 11 to 18% v/v ethanol elution which is eluted with a 11 to 18% v/v ethanol aqueous solution and a fraction of a water elution (2) which is eluted with water. A time of starting collection of peptide SY fraction and times of changing eluents may be determined on the basis of at least one measured value of Bx, salt content, UV (absorption at 280 nm) and Na or on the basis of fractionation time. It is also possible to properly monitor these items in real times and perform the determinations with a computer.

For example, in the elution pattern of FIG. 1, a time of starting fractionation for the latter fraction of the water elution (1) of peptide SY can be determined as follows by measuring a value of a salt content.

i) When the fraction is collected from 0 minute after starting the water elution, the Na content becomes more than 4 g/100 g. Thus, a material having a high Na content is undesirable in view of a blood pressure-depressing agent.

ii) When the collection is performed after 20 minutes from the start-up of the water elution, the permissible range of the Na content is from 1 to 3 g/100 g.

iii) When the collection is started after this time, the Na content is further decreased, but the salt content is too low. Accordingly, guanine contained in peptide SY tends to be precipitated in the concentration, and impurities are sometimes formed which is undesirable.

iv) Consequently, the collection is started after 20 minutes from the start-up of the water elution, and the Na content is approximately 1 to 3 g/100 g.

A final time of collecting the fraction of the water elution (1) is a time when the Na content becomes substantially 0 g/100 g.

Next, from this time, the 11 to 18% v/v ethanol aqueous solution is added instead of water. When the amount of the peptides eluted is past a peak and reduced to approximately a half of the peak, the addition of the ethanol aqueous solution is stopped, and the fraction obtained here is designated a fraction of the 11 to 18% v/v ethanol elution. (Only the fraction of the 11 to 18% v/v ethanol elution is isolated and becomes peptide SY-MD almost free from Na.)

It is advisable that a time when the addition of the 11 to 18% v/v ethanol aqueous solution is stopped and changed to the addition of water is a time when the water elution (2) is started but the UV absorption value at a wavelength of 280 nm showing the total peptide amount starts to be abruptly decreased and reaches approximately a half of the peak, and that an ending time is a time when the UV absorption value reaches zero to enter into a steady state. The fraction obtained here is designated a fraction of the water elution (2).

The product obtained here by collecting (1) the latter fraction of the water elution (1), (2) the fraction of the 11 to 18% v/v ethanol elution and (3) the fraction of the water elution (2) either separately or continuously and mixing them is peptide SY of the invention.

Thus, the fraction including the latter fraction formed during the fractionation for the fraction of the water elution (1), the fraction of the 11 to 18% v/v ethanol elution and the fraction of the water elution (2) in this order can be obtained as peptide SY according to the invention (expressed as sardine peptide SY in FIG. 1).

Further, "15% ethanol elution" shown in FIG. 1 corresponds to peptide SY-MD.

Peptide SY contains a dipeptide (Valyl-Tyrosine; hereinafter sometimes referred to as Val-Tyr or VY) which the present inventors have confirmed for the first time as one of main components of blood pressure-depressing peptides at a high concentration (VY recovery rate: when it is rated as 100% in α-1000, it is from 90 to 95% in SY, whereas it is from 65 to 75% in SY-MD), and shows not only quite a high ACE-inhibiting activity but also a greatly improved taste. However, since peptide SY-MD is free from the latter fraction of the water elution (1), bitterness remains. Since it is almost free from sodium, a useful blood pressure-depressing agent is provided for those who cannot take sodium.

That is, the portion of "solution loading" exhibits a strong taste, but has slight fish odor derived from a raw material and is high in Na content. Meanwhile, the latter fraction of the water elution (1) is reduced in fish odor derived from a raw material, and has quite a good taste.

Accordingly, by incorporating the latter fraction of the water elution (1), a peptide material "peptide SY", from which VY can be recovered in a large amount and is excellent in taste and stability as compared to peptide SY-MD, can be obtained.

Moreover, a blood pressure-suppressing activity as well as functions such as a calcium or iron absorption accelerating function, a cholesterol suppressing function and a blood sugar level decreasing function are confirmed in peptide SY or peptide SY-MD.

The physicochemical properties of peptide SY are as follows.

Physicochemical Properties of Peptide SY
(A) Molecular weight;
200 to 10,000 (FIG. 2)
(B) Melting point; Colored and decomposed at 138±3° C.
(C) Solubility in solvents:
Easily soluble in water, but almost insoluble in ethanol, acetone and hexane.
(D) Appearance:
White or pale yellow powder
(E) Liquid condition (pH): 4.0 to 6.0
(F) Components:
water 1 to 5% w/w (normal-pressure, heat-drying method)
protein 84 to 94% w/w (Micro-Kjeldahl method)
lipid 0.5% w/w or less (Soxhlet extraction method)
ash 4±2% w/w (direct ashing method)
Na 1 to 3% w/w (atomic absorption spectrometry)
(G) Physiological properties:
Containing dipeptide Val-Tyr and having an ACE-inhibiting activity.
(H) Infrared absorption spectrum: FIG. 3
(I) Ultraviolet absorption spectrum: FIG. 4
(J) Specific rotatory power:
$[\alpha]_D^{20} = -40°$ to $-51°$
(K) ACE-inhibiting activity value ($IC_{50}$):
200 μg/ml or less (measured by a Cushman's modification method).

(J) Composition of main amino acids

| Amino acids | Analytical value (%) |
| --- | --- |
| aspartic acid | 8.0 to 9.2 |
| glutamic acid | 9.5 to 12.0 |
| valine | 4.5 to 5.5 |
| methionine | 2.5 to 3.8 |
| isoleucine | 4.5 to 5.2 |
| leucine | 7.3 to 8.5 |
| tyrosine | 3.4 to 4.8 |
| phenylalanine | 4.5 to 5.5 |
| histidine | 3.0 to 3.8 |
| lysine | 6.5 to 7.8 |
| arginine | 5.0 to 6.0 |

(Analytical method: Measured by an amino acid automatic analytical method)

Further, the physicochemical properties of peptide SY-MD are as follows.

Figure 7:
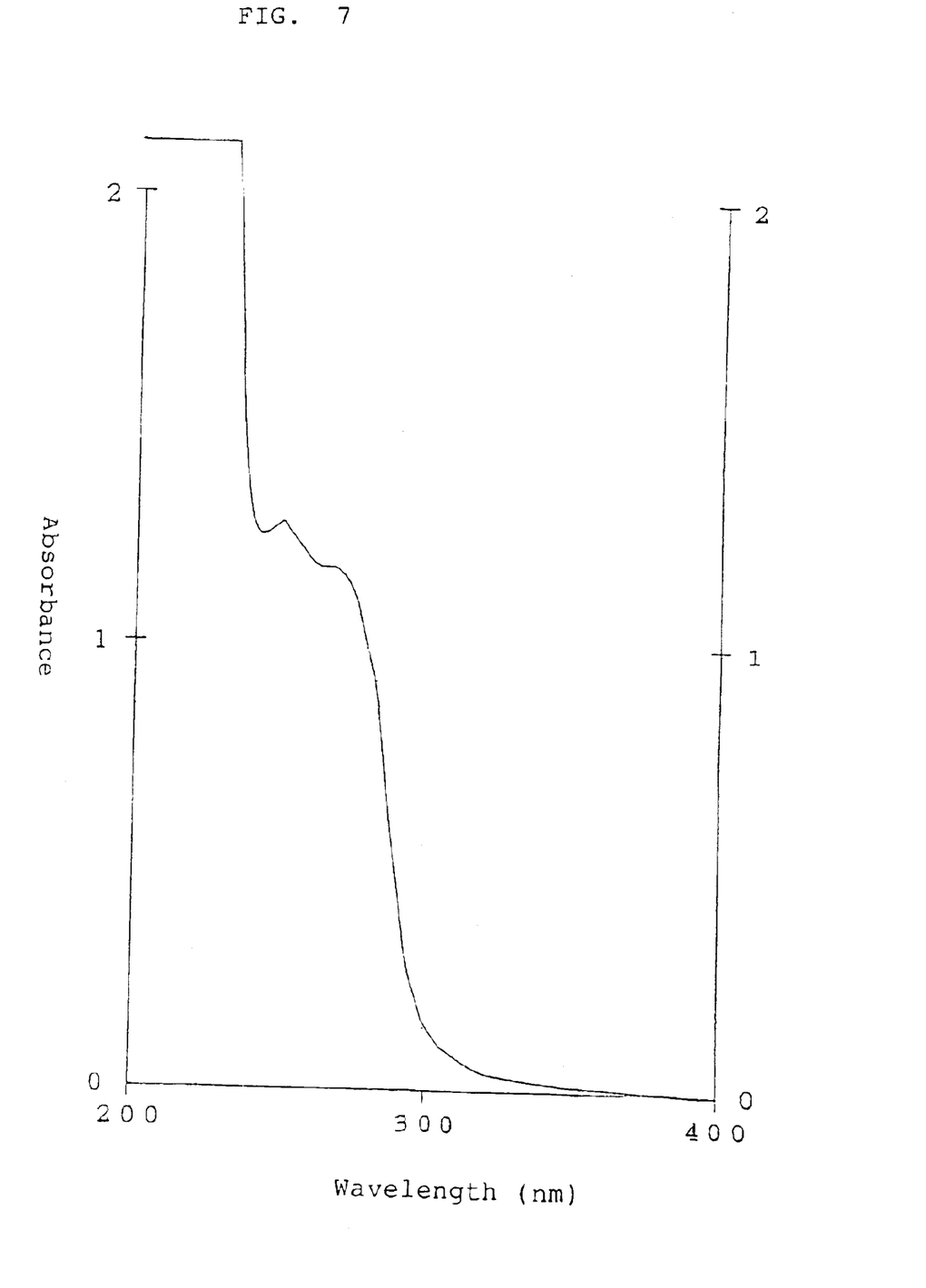
FIG. 7 shows an ultraviolet absorption spectrum of peptide SY-MD (peptide SY-MD is referenced as "peptide SY-peptide Y-2" in FIG. 1). Further, when obtaining peptide SY, a time of starting collection in collecting the FIG. 8 shows an infrared absorption spectrum of peptide SY-MD.
Figure 8:
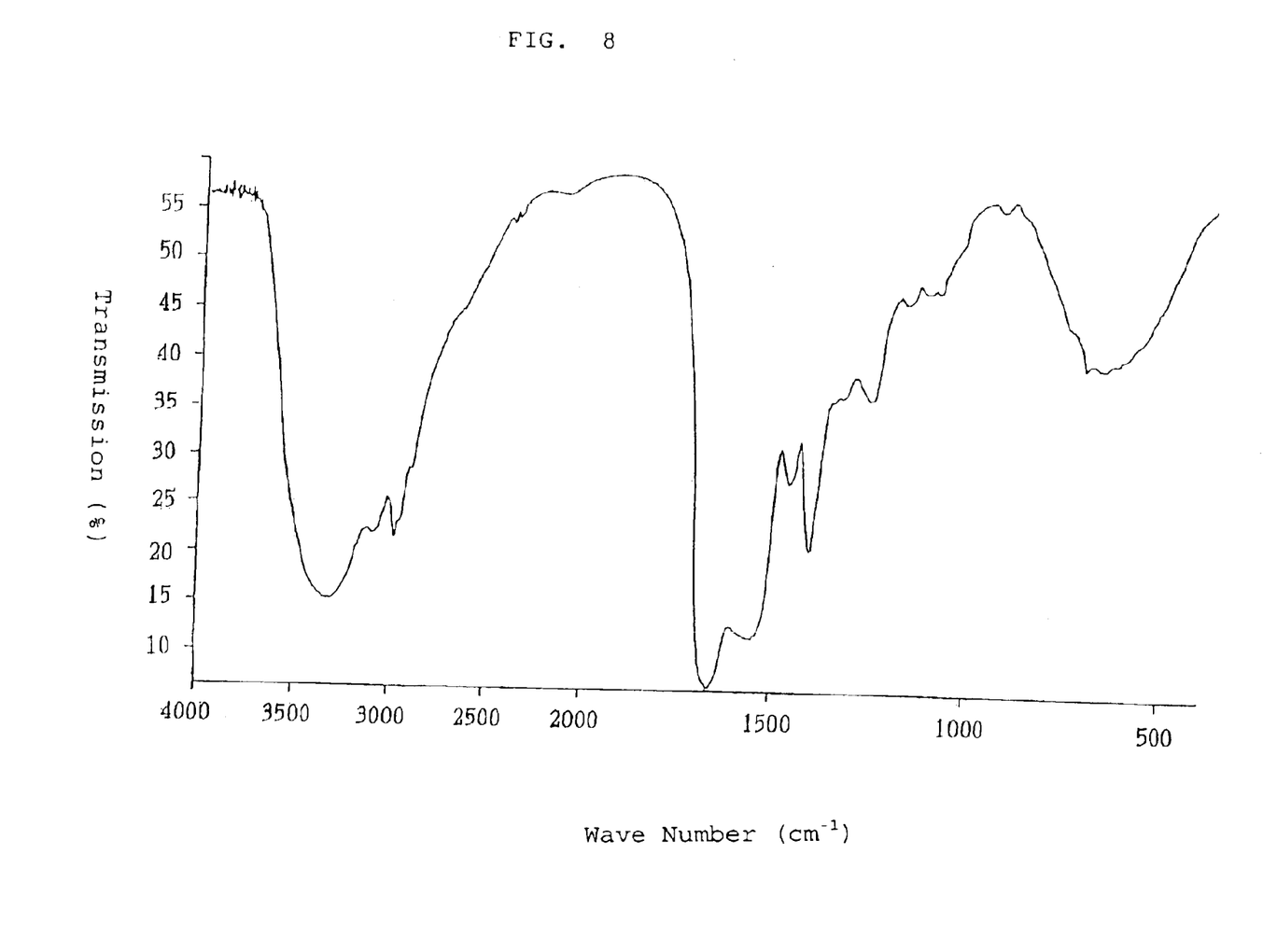

Physicochemical Properties of Peptide SY-MD
(A) Molecular weight;
200 to 10,000
(B) Melting point; Colored and decomposed at 138±3° C.
(C) Solubility in solvents:
Easily soluble in water, but almost insoluble in ethanol, acetone and hexane.
(D) Appearance:
White or pale yellow powder.
(E) Liquid condition (pH): 4.0 to 6.0
(F) Components:
water 2 to 6% w/w (normal-pressure, heat-drying method)
protein 90 to 98% w/w (Micro-Kjeldahl method)
lipid 0.5% w/w or less (Soxhlet extraction method)
ash 3.0% w/w or less (direct ashing method)
Na 0.1 to 0.2% w/w (atomic absorption spectrometry)
(G) Ultraviolet absorption spectrum: FIG. 7
(H) Infrared absorption spectrum: FIG. 8

Peptide SY and peptide SY-MD according to the invention are new peptide mixtures which have been so far unknown. It exhibits an excellent blood pressure-depressing activity, and is not problematic in safety. Accordingly, it can also be used as a mixture of peptides for a blood pressure-depressing agent or foods for specified health use to depress the blood pressure. Therefore, peptide SY and peptide SY-MD can be used as foods or animal feed additives such as seasonings and nutrient supplements, and can also be used widely, because of the foregoing special physiological activities, as medicines or as infusions, health foods and nutrient supplements for clinical use to prevent or treat hypertensive disorders.

Peptide SY and peptide SY-MD can be added, when used as foods, either as such or in combination with other foods or food ingredients in a usual manner as required. Further, the peptide SY and peptide SY-MD can be administered either orally or parenterally when used as medicines. In the oral administration, peptide SY and peptide SY-MD can be formulated into, for example, tablets, granules, particles, capsules, powders or drinks in a usual manner. In the parenteral administration, peptide SY and peptide SY-MD can be used as injections, drops, suppositories or the like.

The invention is illustrated more specifically below by referring to Referential Example and Examples.

REFERENTIAL EXAMPLE

Fresh sardines were processed in a deboner to collect the meat. The meat collected was ground and divided into plural lumps of ground fish meat weighing 10 kg each, and these meat lumps were rapidly frozen at −30° C. or less. Each meat lump was then milled in a mill, and the same amount of water was then added thereto. The mixture was fed into a tank, and heated at 100° C. for 10 minutes to inactivate the autolytic enzyme and thermally denature the meat. Subsequently, aqueous ammonia was added to adjust pH to 9.5.

A 0.1% solution of a commercially-available alkali protease product was added thereto, and the meat was kept at 50° C. for 17.5 hours to conduct decomposition with the enzyme. Then, this was boiled for 15 minutes to inactivate the enzyme.

This was passed through a vibro-screen (150 meshes), treated by Jector at 5,000 rpm, and then processed in a sharpless centrifugal separator (15,000 rpm). This was filtered using a filter aid of diatomaceous earth to provide a peptide solution.

Activated carbon was added to the above-obtained peptide solution in an amount of 1% w/v, stirred at 30° C. for 60 minutes, and then filtered to obtain a filtrate. This filtrate was concentrated under reduced pressure (20° C.) in a usual manner, and then sterilized through UHTST in a usual manner to obtain an α-1000 (liquid) product. This was further spray-dried in a usual manner to obtain α-1000 (powdery) product having a particle size of 60 meshes. These products were frozen and stored respectively.

Example 1

A solution was formed by dissolving 5 g of peptide α-1000 (powder) obtained in Referential Example in 500 ml of deionized water, and passed through a hydrophobic adsorbing resin SEPABEADS SP207 (manufactured by Mitsubishi Chemical Corporation) column (3.5×13 cm) to fill the column with the α-1000 solution (solution loading). Next, according to the elution pattern in FIG. 1, water, a 15% ethanol aqueous solution and water were added in this order in amounts of 500 ml each, and all fractions of sardine peptide SY in FIG. 1, namely, the latter fraction of the water elution (1), the fraction of the 15% ethanol elution and the fraction of the water elution (2) were collected and mixed. The mixture was freeze-dried to obtain 2.1 g of peptide SY (powder). The Na content of peptide SY was 1.45% w/w (measured by atomic absorption spectrometry).

Example 2

A solution was formed by dissolving 5 g of peptide α-1000 (powder) obtained in Referential Example in 500 ml of deionized water, and passed through a hydrophobic adsorbing resin SEPABEADS SP207 (manufactured by Mitsubishi Chemical Corporation) column (3.5×13 cm) to fill the column with the α-1000 solution (solution loading). Among all the fractions of sardine peptide SY shown in the elution pattern of FIG. 1, only the fraction of the 15% ethanol elution was isolated and collected. This was freeze-dried to obtain 1.7 g of peptide SY-MD (powder). The Na content of peptide SY-MD was 0.124% w/w (measured by atomic absorption spectrometry).

Example 3

(Preparation of drinks)

| Table of formulation of 100-ml drink | |
|---|---|
| liquid fructose-glucose | 4.5 g |
| sugar alcohol | 1 g |
| sour | 0.2 g |
| flavoring | 0.13 g |
| sweetener (stevia) | 0.03 g |
| caramel dye | 0.02 g |
| peptide SY (powder) | 0.5 g |

(obtained in Example 1)
purified water to adjust the total volume to 100 ml

| Table of formulation of 50-ml drink | |
|---|---|
| liquid fructose-glucose | 10 g |
| flavoring | 0.3 g |
| sour | 0.16 g |
| sweetener (stevia) | 0.015 g |
| peptide SY (powder) | 0.5 g |

(obtained in Example 1)
purified water to adjust the total volume to 50 ml

| Table of formulation of 30-ml drink | |
|---|---|
| liquid fructose-glucose | 5 g |
| flavoring | 0.25 g |
| sour | 0.1 g |
| sweetener (stevia) | 0.015 g |
| peptide SY (powder) | 0.5 g |

(obtained in Example 1)
purified water to adjust the total volume to 30 ml

The foregoing components were mixed and dissolved at 60° C., and then subjected to plate sterilization at 128° C. for 10 seconds. The resulting mixtures were then filled at 90° C. into 100-ml, 50-ml and 30-ml well-washed brown bottles. The bottles were allowed to cool at room temperature, and then rapidly cooled with running water in a bath to prepare drinks.

Example 4

(Preparation of tablets)

Tablets were prepared according to the following formulation.

500 g of peptide SY (powder) obtained in Example 1, 356 g of a reducing maltose thick syrup, 100 g of crystalline cellulose, 40 g of sucrose fatty acid ester and 4 g of a sweetener (stevia) were mixed, and this mixture was compressed with a compression tablet machine to form raw tablets (250 mg ×4,000 pieces). The raw tablets were coated with a shellac solution in an amount of 7.5 mg per tablet to prepare 4,000 tablets containing peptide SY (powder) in an amount of 500 mg per 4 tablets.

Example 5

Examples of administering the drinks prepared in Example 3 are described.

(1) In Case of the 30-ml Drink

Peptide SY was used in an amount of 0.5 g/drink. Persons suffering from light hypertension were divided into a peptide administration group and a placebo group according to a random double blind test to perform a clinical examination. Each of them took one drink every day. After 4 weeks, the upper blood pressure of only the peptide administration group was significantly reduced by 10.6 mmHg, and the lower blood pressure thereof by 5.6 mmHg respectively in terms of an average value.

(2) In Case of the 50-ml Drink

Likewise, persons suffering from light hypertension were divided into a peptide administration group and a placebo group according to a random double-blind test to perform a clinical examination. Each of them took one drink every day. After 4 weeks, the upper blood pressure of only the peptide administration group was significantly reduced by 10.2 mmHg, and the lower blood pressure thereof by 3.8 mmHg respectively in terms of an average value.

(3) In Case of the 100-ml Drink

Likewise, a clinical examination was performed. After 4 weeks, the upper blood pressure of only the peptide administration group was significantly reduced by 8.2 mmHg, and the lower blood pressure thereof by 3.0 mmHg respectively in terms of an average value.

Consequently, in all cases, by taking the drink containing 0.5 g/drink of peptide SY once a day, the blood pressure of the persons suffering from light hypertension was significantly decreased at a significance level of 1% or less without affecting subjective and objective symptoms.

Example 6

An example of administering the tablets prepared in Example 4 is described.

A placebo control double-blind administration test was performed for 88 persons who were persons having a normal high blood pressure and persons suffering from light hypertension.

They took the tablets at a dose of 4 tablets a day (0.5 g/day as peptide SY). Consequently, in the peptide SY administration group (44 persons), the upper blood pressure (systolic blood pressure) was 148±11 mmHg and the lower blood pressure (diastolic blood pressure) was 92±14 mmHg at the start-up of the test, whereas the upper blood pressure was significantly decreased to 138±12 mmHg after 4 weeks and to 134±9 mmHg after 8 weeks, and the lower blood pressure was significantly decreased to 84±11 mmHg after 4 weeks and 83 ±10 mmHg after 8 weeks. In the placebo group (44 persons), no significant change was found. Further, side effects such as dry cough were not observed at all in any of these groups. Thus, the blood pressure-depressing effect of the tablets containing peptide SY was confirmed among the persons having the normal high blood pressure and the persons suffering from light hypertension.

Example 7

(Preparation of drink)

Table of formulation of 100-ml drink

| | |
|---|---|
| liquid fructose-glucose | 4.5 g |
| sugar alcohol | 1 g |

-continued

Table of formulation of 100-ml drink

| | |
|---|---|
| sour | 0.2 g |
| flavoring | 0.13 g |
| sweetener (stevia) | 0.03 g |
| caramel dye | 0.02 g |
| peptide SY-MD (powder) | 0.5 g |

(obtained in Example 2)

purified water to adjust the total volume to 100 ml

This 100-ml drink contained peptide SY-MD at a dose of 500 mg/drink, and the components were: water 96.7 g, protein 0.5 g, sugar 4.5 g, heat value 19 Kcal, sodium 7.4 mg and sorbitol 0.66 g.

A double-blind comparison test was performed using one drink containing 0.5 g/drink of this peptide SY-MD a day for volunteers, namely, persons having a normal high blood pressure with a systolic blood pressure of from 130 to 140 mmHg and a diastolic blood pressure of from 80 to 90 mmHg, and persons suffering from light hypertension with a systolic blood pressure of from 140 to 160 mmHg and a diastolic blood pressure of from 90 to 100 mmHg.

As a result, in the placebo drink administration group, no significant difference was found in the change of the blood pressure, whereas in the peptide drink administration group, after 4 weeks, the systolic blood pressure was significantly decreased by 14.7 mmHg and the diastolic blood pressure by 7.6 mmHg as compared to those before the administration. Thus, the effectiveness of peptide SY-MD was confirmed.

Example 8

(Preparation of tablets)

Tablets were prepared according to the following formulation.

500 g of peptide SY-MD (powder) obtained in Example 2, 356 g of a reducing maltose thick syrup, 100 g of crystalline cellulose, 40 g of sucrose fatty acid ester and 4 g of a sweetener (stevia) were mixed, and this mixture was compressed with a compression tablet machine to form raw tablets (250 mg ×4,000 pieces). The raw tablets were coated with a shellac solution in an amount of 7.5 mg per tablet to prepare 4,000 tablets containing peptide SY-MD (powder) in an amount of 500 mg per 4 tablets.

The components thereof were: water 3.3 g, protein 44.2 g, sugar 3.5 g, ash 1.6 g, carbohydrate 47.4 g and sodium 566 mg, per 100 g, and a heat value was 398 Kcal.

A double-blind comparison test was performed for 12 weeks using the tablets at a dose of 4 tables/day (administering 0.5 g/day as peptide SY-MD) and placebo free from peptide SY-MD as a control. Among 40 volunteers who were persons having a normal high blood pressure and persons suffering from light hypertension, the group of administering the peptide SY-MD containing tablets showed the significant blood pressure depression in both the systolic blood pressure (SBP) and the diastolic blood pressure (DBP) as compared to those before the administration. That is, before the administration, SBP was 145.4 mmHg and DBP 86.8 mmHg, whereas in the end of the test, SBP was 134.7 mmHg and DBP 83.0 mmHg. In the placebo group, no significant change in blood pressure was observed. Throughout 12 weeks, subjective symptoms such as side effects did not occur.

Effects of the Invention

Peptide SY and peptide SY-MD according to the invention are excellent in blood pressure-depressing function because each contains Val-Tyr found as a blood pressure-depressing component, namely, a main component of a blood pressure-depressing peptide at a high concentration. Further, by incorporating a part of a fraction of water elution, peptide SY has characteristics that it is free from bitterness and excellent in taste and stability. Since the novel and extremely effective peptide SY according to the invention has the foregoing characteristics, it can be used not only as foods and drinks per se or as additives, but also as health foods for inhibiting or preventing the blood pressure elevation because of the excellent ACE-inhibiting activity. Moreover, it can advantageously be used as agents such as an ACE-inhibiting agent and a blood pressure-depressing agent by being formulated into various dosage forms.

The novel peptide SY and peptide SY-MD exhibit, as is clear from the foregoing description, the excellent blood pressure-depressing activity. Further, they are derived from fish meat and therefore they do not give rise to a problem in safety (in reality, when each was forcibly administered orally to rats at a dose of 500 mg/day, no acute toxicity was observed even after 10 days). Accordingly, each can be used as a mixture of peptides for a blood pressure-depressing agent or for foods for specified health use in depressing the blood pressure.

What is claimed is:

1. A Peptide SY having the following physicochemical properties.

(A) Molecular weight:
   200 to 10,000 (measured by high-performance liquid chromatography: ASAHIPAK GS-320)
   (B) Melting point: Colored and decomposed at 138±3° C.
   (C) Solubility in solvents:
   Easily soluble in water, but almost insoluble in ethanol, acetone and hexane
   (D) Appearance:
   White or pale yellow powder
   (E) Liquid condition (pH): 4.0 to 6.0
   (F) Components:
   water 1 to 5% w/w (normal-pressure, heat-drying method)
   protein 84 to 94% w/w (Micro-Kjeldahl method)
   lipid 0.5% w/w or less (Soxhlet extraction method)
   ash 4±2% w/w (direct ashing method)
   Na 1 to 3% w/w (atomic absorption spectrometry)
   (G) Physiological properties:
   Containing dipeptide Val-Tyr and having an ACE-inhibiting activity
   (H) Infrared absorption spectrum: FIG. 3
   (I) Ultraviolet absorption spectrum: FIG. 4.

2. The Peptide SY as claimed in claim 1, which is produced by collecting and mixing peptide components resulting from elution fractionation of a peptide solution with a peptide-adsorbing resin using water, an ethanol aqueous solution and water in this order as eluents of the elution fractionation, in which the peptide components are, in an elution pattern shown in FIG. 1, a latter fraction of the water elution (1), a fraction of the 11 to 18% v/v ethanol elution and a fraction of the water elution (2) obtained by the respective eluents as defined below:

(1) Latter fraction of the water elution (1): Fraction obtained using water as an eluent from a time when a sodium (Na) content of the whole elution peptide fraction (peptide SY) is from 1 to 3 g/100 g to a final collection time of the latter fraction in the water elution (1) when the sodium content is substantially 0 g/100 g;

(2) Fraction of the ethanol elution: Fraction obtained next using the ethanol aqueous solution having a concentration of 11 to 18% v/v as an eluent until an amount of peptide eluted is past a peak and reduced to approximately a half of the peak;

(3) Fraction of the water elution (2): Fraction thereafter obtained using water as an eluent until the elution fractionation is completed.

3. The Peptide SY as claimed in claim 1, which is produced using an aqueous solution of peptide α-1000 derived from fish meat and having the following physicochemical properties as a peptide solution:

(a) Molecular weight;
   200 to 10,000 (measured by Sephadex G-25 column chromatography)
   (b) Melting point;
   Colored at 119° C. (decomposition point)
   (c) Specific rotatory power
   $[\alpha]_D^{20}=-22°$
   (d) Solubility in solvents;
   Easily soluble in water, but almost insoluble in ethanol, acetone and hexane.
   (e) Differentiation in acidic, neutral or basic character;
   Neutral
   (f) Appearance, Components;
   White powder: water 5.14% (reduced-pressure, heat-drying method); protein 87.5% (Kjeldahl method with a nitrogen/protein conversion coefficient of 6.25); lipid 0% (Soxhlet extraction method); ash 5.0% (direct ashing method).
   (g) Characteristic;
   Mixture of peptides derived from fish meat and obtained by heating the fish meat to inactivate its autolytic enzyme and hydrolyzing the resulting meat with a protease.

4. A process for producing a peptide SY-MD comprising collecting and mixing peptide components resulting from elution fractionation of a peptide solution with a peptide-adsorbing resin using water, then isolating and collecting only a fraction obtained using an ethanol aqueous solution having a concentration of 11 to 18 % v/v as an eluent until an amount of peptide eluted is past a peak and reduced to approximately a half of the peak.

5. A blood pressure-depressing agent comprising, as an active ingredient, the peptide SY as claimed in claim 1.

6. A blood pressure-depressing functional food comprising the peptide SY as claimed in claim 1.

7. The food as claimed in claim 6, wherein the food is in a liquid or solid form.

8. The peptide SY as claimed in claim 2, which is produced using an aqueous solution of peptide α-1000 derived from fish meat and having the following physicochemical properties as a peptide solution:

(a) Molecular weight;
   200 to 10,000 (measured by Sephadex G-25 column chromatography)
   (b) Melting point;
   Colored at 119° C. (decomposition point)
   (c) Specific rotatory power
   $[\alpha]_D^{20}=-22°$
   (d) Solubility in solvents;
   Easily soluble in water, but almost insoluble in ethanol, acetone and hexane
   (e) Differentiation in acidic, neutral or basic character;
   Neutral (f) Appearance, Components;

White powder: water 5.14% (reduced-pressure, heat-drying method); protein 87.5% (Kjeldahl method with a nitrogen/protein conversion coefficient of 6.25); lipid 0% (Soxhlet extraction method); ash 5.0% (direct ashing method)

(g) Characteristic;

Mixture of peptides derived from fish meat and obtained by heating the fish meat to inactivate its autolytic enzyme and hydrolyzing the resulting meat with a protease.

* * * * *